United States Patent
Bain et al.

(10) Patent No.: US 11,491,328 B2
(45) Date of Patent: *Nov. 8, 2022

(54) PREVENTION AND TREATMENT OF DIASTOLIC FLOW REVERSAL

(71) Applicants: Duncan Bain, Hertfordshire (GB); Arthur Tucker, London (GB); Bernard Ross, Liverpool (GB)

(72) Inventors: Duncan Bain, Hertfordshire (GB); Arthur Tucker, London (GB); Bernard Ross, Liverpool (GB)

(73) Assignee: Sky Medical Technology, Ltd., Liverpool (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/652,687

(22) Filed: Jul. 18, 2017

(65) Prior Publication Data

US 2017/0312493 A1 Nov. 2, 2017

Related U.S. Application Data

(60) Continuation of application No. 14/677,295, filed on Apr. 2, 2015, now Pat. No. 9,731,107, which is a
(Continued)

(30) Foreign Application Priority Data

Dec. 19, 2008 (GB) .................. 08232134

(51) Int. Cl.
*A61N 1/36* (2006.01)
*A61N 1/04* (2006.01)
(Continued)

(52) U.S. Cl.
CPC .......... *A61N 1/205* (2013.01); *A61N 1/0452* (2013.01); *A61N 1/36003* (2013.01);
(Continued)

(58) Field of Classification Search
CPC .. A61N 1/205; A61N 1/0452; A61N 1/36003; A61N 1/36103; A61N 1/36067
(Continued)

(56) References Cited

U.S. PATENT DOCUMENTS 4,976,264 A 12/1990 Petrofsky
5,643,331 A 7/1997 Katz
(Continued)

FOREIGN PATENT DOCUMENTS

DE 3916994 A1 11/1990
JP 2001-54507 2/2001
(Continued)

OTHER PUBLICATIONS

English translation of Request for Invalidation of Patent Rights of Chinese Patent No. 2005800466617.

*Primary Examiner* — Jon Eric C Morales

(74) *Attorney, Agent, or Firm* — Raymond J. Lillie

(57) ABSTRACT

Methods and devices are described for preventing diastolic flow reversal and/or reducing peripheral vascular resistance in a patient. Also described are methods of cosmetic treatment, and methods of promoting delivery of therapeutic agents or contrast agents to bones and related tissues.

4 Claims, 13 Drawing Sheets

Related U.S. Application Data division of application No. 13/138,268, filed as application No. PCT/GB2009/051713 on Dec. 15, 2009, now Pat. No. 9,707,387.

(51) Int. Cl.
 *A61N 1/20* (2006.01)
 *A61N 1/39* (2006.01)

(52) U.S. Cl.
 CPC ....... *A61N 1/36034* (2017.08); *A61N 1/3904* (2017.08); *A61N 1/36067* (2013.01); *A61N 1/36103* (2013.01)

(58) Field of Classification Search
 USPC .......................................................... 607/48
 See application file for complete search history.

(56) References Cited

U.S. PATENT DOCUMENTS

| | | | |
|---|---|---|---|
| 5,674,262 A | 10/1997 | Tumey | |
| 5,755,750 A * | 5/1998 | Petruska | A61N 1/0551 607/118 |
| 6,445,955 B1 | 9/2002 | Michelson et al. | |
| 6,615,080 B1 | 9/2003 | Unsworth | |
| 9,707,387 B2 * | 7/2017 | Bain | A61N 1/36034 |
| 2002/0087201 A1 | 7/2002 | Firlik | |
| 2003/0083698 A1 | 5/2003 | Whitehurst | |
| 2003/0144709 A1 | 7/2003 | Zabara | |
| 2004/0172097 A1 | 9/2004 | Brodard | |
| 2005/0080463 A1 | 4/2005 | Stahmann | |
| 2007/0060862 A1 | 3/2007 | Sun et al. | |
| 2007/0293917 A1 | 12/2007 | Thompson et al. | |
| 2008/0065182 A1 * | 3/2008 | Strother | A61N 1/378 607/115 |
| 2008/0077192 A1 | 3/2008 | Harry et al. | |
| 2008/0207985 A1 | 8/2008 | Farone | |
| 2009/0048651 A1 * | 2/2009 | Andino | A61N 1/0468 607/115 |
| 2009/0319003 A1 | 12/2009 | Castel | |
| 2011/0087300 A1 | 4/2011 | Van Den Eerenbeemd et al. | |
| 2012/0041513 A1 * | 2/2012 | Tucker | A61N 1/36034 607/48 |

FOREIGN PATENT DOCUMENTS

| | | |
|---|---|---|
| JP | 2007-503286 | 2/2007 |
| UA | 28849 | 12/2008 |
| WO | WO99/064105 | 12/1999 |
| WO | WO01/51123 | 7/2001 |
| WO | WO03/063960 | 8/2003 |
| WO | WO2006/054118 | 5/2006 |
| WO | WO2007/050657 | 5/2007 |
| WO | WO2008/045598 | 4/2008 |
| WO | WO2008/088985 | 7/2008 |
| WO | WO2008/103977 | 8/2008 |
| WO | WO2008/106077 | 9/2008 |

* cited by examiner

SECTION E-E

PREVENTION AND TREATMENT OF DIASTOLIC FLOW REVERSAL

This application is a continuation of application Ser. No. 14/677,295, filed Apr. 2, 2015, which is a divisional of application Ser. No. 13/138,268, filed Nov. 4, 2011, now U.S. Pat. No. 9,707,387, which is the national stage application of PCT Application No. PCT/GB2009/051713, filed Dec. 15, 2009, which claims priority based on United Kingdom Application No. 0823213.4, filed Dec. 19, 2008, the contents of which are incorporated by reference in their entireties.

FIELD OF THE INVENTION

The present invention relates to a method and device for medical and/or cosmetic treatment. In particular, one aspect of the invention relates to a method for reducing peripheral vascular resistance in the blood circulation of a patient; other aspects of the invention relate to methods of treatment of disorders characterised by increased peripheral vascular resistance. The invention also relates to a device for implementing the method. Further aspects of the invention relate to other uses of the device.

BACKGROUND OF THE INVENTION

A method and device for reduction or treatment of deep vein thrombosis (DVT) are described in international patent application WO2006/054118. This device includes electrodes which are secured to the leg of a patient and used to provide electrical stimulation to the muscles. Preferably the electrodes are arranged to stimulate the lateral and/or medial popliteal nerves, which causes the calf muscles to contract. This in turn activates the calf musculovenous pump, in which blood circulation is promoted by muscle contraction, so serving to reduce the risk of thrombosis in the limb. Other musculovenous pumps include the foot pump, and the device may be used to stimulate this as well as, or instead of, the calf pump. The device is preferably used to induce isometric contraction of the muscles, such that the musculovenous pumps may be activated but limb movement from the stimulation is reduced or avoided.

As described in WO2006/054118, use of the device in the manner described has been demonstrated to increase venous emptying in the leg, as well as to increase cortical blood flow in the long bones of the leg. Due to these effects, the device is suggested for use to treat conditions other than DVT characterised by impaired venous blood flow, including ulcers, varicose veins, ischaemia, oedema, phlebitis, osteoporosis, peripheral vascular disease, coronary heart disease, and hypertension. These disorders are considered to be treatable on the basis that the device and method can increase venous blood flow.

We have now surprisingly determined that the device, and similar devices, may be used to alter the patterns of blood flow in a patient.

SUMMARY OF THE INVENTION

We present here evidence that electrical stimulation of muscles may be used not only to activate the calf musculovenous pump to increase venous emptying, but also to alter the patterns of blood flow in a patient. In particular, diastolic flow reversal in the artery may be reduced or even prevented. This is thought to be a consequence of a reduction in peripheral vascular resistance. While enhancing blood flow was previously known, the finding that blood flow may be significantly altered is unexpected, and offers several novel ways in which the device may be used.

According to a first aspect of the present invention, there is provided a method of reducing peripheral vascular resistance in a leg of a patient, the method comprising administering one or more electrical stimuli to a plurality of leg muscles sufficient to cause isometric contraction of the muscles. Also provided is a method of reducing or preventing diastolic flow reversal in an artery in a leg of a patient, the method comprising administering one or more electrical stimuli to a plurality of leg muscles sufficient to cause isometric contraction of the muscles.

The reduction of peripheral vascular resistance, and the reduction of diastolic flow reversal, allow for the treatment of additional conditions which were not previously known to be treatable by electrical stimulation of muscles. In particular, the invention also provides a method for treatment of disorders characterised by increased peripheral vascular resistance. Such disorders include lower limb arterial, disease (peripheral arterial disease); impaired lower limb lymphatic drainage; cardiac diseases; restless leg syndrome (Wittmaack-Ekbom's syndrome); soft tissue injury of the lower limb (including skin and muscle bruising and micro tears; and sports injuries); and inflammation. The invention provides methods for treatment of each of these disorders. The reduction of peripheral vascular resistance is also thought to be of benefit in sports training and rehabilitation, whether or not the subject has an injury.

For example, the methods of the invention may be used to reduce recovery time after a sports event. After such an event, for example, a football match, or an athletics race, even if a participant is not injured, their performance may take several days to recover to the pre-event level. We believe that the method of the invention may be of benefit in reducing this recovery time; for example, if applied from 2-24 hours after an event, or between training sessions.

The method may also be of benefit in other conditions in which blood pooling may be a problem. In particular, for prevention or avoidance of G-LOC (g-force induced loss of consciousness). In such an embodiment, the method may also comprise the steps of monitoring g-force experienced by a subject, and adjusting the stimuli in response to variations in the monitored g-force (for example, an increased g-force may result in an increased frequency of stimulation). Other applications include maintaining blood flow in reduced gravity, for example, during space travel; reducing the likelihood of blood pooling during prolonged periods of standing (for example, among soldiers on parade); or reducing or avoiding blackouts experienced on sudden standing.

The leg muscles are preferably the calf muscle, although in certain embodiments of the invention, stimulation of the ankle and/or foot musculature may instead or in addition be used. The leg muscles are preferably involved in a musculovenous pump; for example, the calf, foot, and/or thigh pumps.

The stimuli may be applied directly to the muscles, or indirectly via stimulation of a suitable nerve. For example, a favoured approach is to indirectly stimulate the lower limb musculature by accessing nerve groups in the area of the popliteal fossa, where the nerve groups are in general easily accessible in individuals, regardless of body mass, and with minimum energy requirement. Unless otherwise specified, it will be appreciated that all reference herein to stimulation of a muscle is intended to encompass both direct stimulation and indirect stimulation.

A possibly undesirable effect of isolated contraction of the calf muscles is the plantar-flexion of the foot. In a seated individual this may cause the knee to rise, so making the process more obtrusive. Isometric contraction ensures that opposing muscles or groups of muscles are, stimulated such that there is no or little movement of the limb as a result. The stimulus may be applied directly to posterior calf muscles; conveniently the soleus and/or gastrocnemius muscles. Indirect stimulation of the lower limb muscles may be achieved by electrical stimulation of the lateral popliteal nerve in the region of the popliteal fosse. Specifically at the inner margin of the biceps femoris muscle, behind the fibula at the inner side of the tendon of the biceps femoris. Additionally, indirect stimulation of the lower limb muscles may be further achieved by electrical stimulation of the medial popliteal nerve, which is located medially from the lateral popliteal nerve in the region of the popliteal fosse.

A second stimulus may be applied to shin muscles; conveniently the tibialis anterior. Preferably the second stimulus is applied simultaneously to the stimulus applied to the calf muscles. Stimulation, of the tibial muscle alone will promote blood flow to some extent, although the primary purpose of this second stimulation is to prevent unwanted limb movement. Application of a stimulus only to a posterior calf muscle may have the unwanted side effect of causing movement of the ankle joint. Application of a stimulus to the shin muscle will counteract any movement of the ankle joint caused by contraction of the calf muscle, so keeping the ankle and knee joints relatively still.

Alternatively, stimulation of, the lateral popliteal nerve, in the region of the popliteal fossa, has the advantage of initiating the contraction of both posterior and anterior lower limb muscle groups from a single stimulation point. Such simultaneous stimulation results in isometric contraction; hence the ankle and knee joints would not be typically mobilised. Stimulation of the lateral popliteal also elicits contraction of the foot muscles and hence, the so-called "foot-pump". Additionally, the surprising advantage of selective stimulation of the lateral popliteal nerve is that the resultant muscular contractions are entirely compatible withstanding and walking. An additional benefit of this mode of indirect stimulation is the involvement of the muscles in the sole of the foot which have been shown to contributed substantially to clearance of blood from the lower leg. It has further been identified that stimulation of the nerve in this way, rather than the muscles directly, allows the method to be operated so as to engender little or no noticeable skin sensation or discomfort when used to stimulate muscle contraction:

In a clinical environment, where standing and walking are not a pre-requisite, the medial popliteal nerve may be stimulated, either in isolation or in combination with stimulation of the lateral popliteal nerve. A preferred version of dual medial and lateral popliteal nerve stimulation may result in near maximal contraction of the entire lower limb musculature, leading to enhanced efficiency and activity of both the calf and foot venous pumps, and by extension, movement of venous blood out of the lower limb, centrally towards the abdomen.

The method preferably comprises repeatedly administering an electrical stimulus to the muscles.

A typical electrical stimulus may be at a current of between 0 to 100 mA, preferably 0 to 50 mA, more preferably 1 to 40 mA, and most preferably between 1 to 20 mA. Other examples of stimulus currents include between 15 and 30 mA.

The stimulus may be an AC waveform, although it is preferably a DC waveform, more preferably a pulsed DC waveform. The stimulus may have a frequency of 0.01 to 100 Hz, preferably 0.1 to 80 Hz, more preferably 0.1 to 50 Hz; and more preferably still 0.1 to 5 Hz. The most preferred frequencies are 0.5-5 Hz, 1-5 Hz, preferably 1-3 Hz; for example, 1, 2 or 3 Hz. In other embodiments, the frequency may be from 30 to 60 Hz, and more preferably 40 to 50 Hz. Alternatively, a stimulus with a frequency from 0.1 to 1 Hz, or from 0.33 to 1 Hz may be used. The precise desired frequency may depend on the purpose of the method, the desired physiological mode of action it is intended to cause, and the general physical condition, age, sex, and weight of the patient, among other factors.

Specific examples of preferred stimuli include 20 mA, at a frequency of 5 Hz, 30 mA at 3 Hz, and 28 mA at 1 Hz. Other stimuli may of course be used.

The stimulus may be applied for a duration between 0 and 1000 ms, between 100 and 900 ms, between 250 and 750 ms, between 350 and 650 ms, or between 450 and 550 ms. In certain embodiments, the stimulus may be applied for up to 5000 ms, up to 4000 ms, up to 3000 ms, or up to 2000 ms. Other durations may be used; again this may depend on the details of the patient or the mode of action intended. Other preferred durations include from 70 to 600 ms. In certain embodiments, yet shorter durations may be used, for example from 25 µs to 800 µs.

Characteristics of the stimulus may vary over time. For example, a single stimulus may increase in current over the duration of the stimulus. Preferably the increase is gradual up to a peak; the stimulus may then either be maintained at the peak; terminate at the peak; or degrease in a gradual manner. Alternatively, where repeated stimuli are applied, characteristics of the stimuli may vary between different stimuli. For example, successive stimuli may be applied at increasing levels of current. Again, these successive stimuli may increase up to a peak gradually, followed by maintenance at that peak, or decrease from the peak. A cycle of increasing stimuli may be repeated a number of times. In preferred embodiments, each stimulus is a single pulse, rather than multiple brief pulses.

Stimuli may be applied at a plurality of locations on the muscles. For example, stimuli may be applied along the main (long) axis of the leg. Such stimuli may be applied simultaneously, or preferably sequentially such that a 'wave' of stimuli proceeds along the leg. Preferably, such a wave proceeds upward toward the body of the patient. This wave effect serves to generate a corresponding wave of muscle contraction which wave may help to promote blood flow away from the leg. However, in preferred embodiments of the invention a stimulus is applied at a single point on the leg, to stimulate the lateral popliteal fossa nerve, as described above. "A single point" may include stimulation by more than one electrode, for example, a pair of positive and negative electrodes, with a sufficiently small separation (for example, 1-3 cm, or up to 2 cm) such that the stimulation is experienced at a point by the user rather than over a larger area.

Also provided is a method for diagnosing conditions characterised by increased peripheral, vascular resistance, the method comprising administering one or more electrical stimuli at a first frequency and/or current to a plurality of leg muscles sufficient to cause isometric contraction of the muscles; and monitoring blood flow in the leg to determine whether diastolic reversal of arterial flow is reduced or prevented and/or peripheral vascular resistance is reduced.

The method may further comprise repeating the stimulation and monitoring steps at a second frequency and/or current, and determining the level of frequency and/or current required to effect reduction or prevention of diastolic reversal of arterial flow; and/or reduction of peripheral vascular resistance. The level at which this occurs may give some information as to the severity of the condition.

The method may further comprise comparing the level of frequency and/or current required to effect reduction or prevention of diastolic reversal of arterial flow and/or reduction of peripheral vascular resistance with the levels required in a healthy control patient. Again, this may help diagnose a condition or give some indication as to the severity of the condition. The healthy control patient may be selected so as to be otherwise comparable to the patient.

Also provided according, to the present invention is a method for promoting circulation in a patient having a heart condition, the method comprising administering one or more electrical stimuli to a plurality of leg muscles sufficient to cause isometric contraction of the muscles. As noted above, electrical stimulation of the musculovenous pump promotes altered blood flow patterns, which may be beneficial in patients having heart conditions. The heart condition may include cardiac arrest, suspected cardiac arrest, arrhythmia, brachycardia, or angina. The method may also be used as an adjunct to defibrillation in the case of cardiac arrest. Also provided is a device for use in promoting circulation in a patient having a heart condition, the device comprising at least one electrode for administering an electrical stimulus to opposed leg muscles of a patient; a power supply connectable to the electrode; and a control means for activating the electrode to administer an electrical stimulus to the muscles sufficient to cause the muscles to contract isometrically. The invention also provides a kit comprising such a device in combination with a defibrillator. Alternatively, the device may include a defibrillator.

Further aspects of the present invention relate to the modification of cortical blood flow in bone. As noted in WO2006/054118, the method of isometric muscle stimulation has been shown to promote cortical blood flow. We have since discovered, and demonstrate herein, that bone oxygenation and bone perfusion are increased by use of the method. This allows more effective delivery of pharmaceutical agents to the bone, particularly those intended for treatment of bone disorders including osteoporosis. Thus, according to a further aspect of the present invention there is provided a method for improving administration of medicaments for treatment of bone disorders, the method comprising administering said medicament to a patient, and administering one or more electrical stimuli to a plurality of leg muscles sufficient to cause isometric contraction of the muscles and enhance bone perfusion. The bone disorder may be osteoporosis. Also provided is a kit for treatment of bone disorders, the kit comprising a medicament for treatment of a bone disorder and a device comprising at least one electrode for administering an electrical stimulus to opposed leg muscles of a patient; a power supply connectable to the electrode; and a control means for activating the electrode to administer an electrical stimulus to the muscles sufficient to cause the muscles to contract isometrically.

Improved perfusion may also be useful for improving delivery of contrast agents (for example for medical imaging purposes) to tissues such, as the bones, tendons, ligaments, etc. An aspect of the invention therefore provides a method for improving delivery of contrast agents, the method comprising administering said contrast agent to a patient, and administering one or more electrical stimuli to a plurality of leg muscles sufficient to cause isometric contraction of the muscles and enhance perfusion of said agent.

A still further aspect of the invention relates to cosmetic therapy. As demonstrated herein, use of the method increases peripheral blood circulation, in particular circulation in the skin. The method also increases skin temperature where circulation is increased. These effects may be of benefit in the cosmetic treatment of individuals. For example, the effects may include reduction of cellulite or collagen deposits, improvement of skin tone, or improvement of skin condition. Thus, the invention provides a method for cosmetic treatment of a patient, the method comprising administering an electrical stimulus 'to at least one leg muscle of a patient sufficient to cause the muscles to contract' isometrically. The cosmetic treatment may be selected from reduction of cellulite or collagen deposits, improvement of skin tone, or improvement of skin condition. Also provided is a kit for beauty therapy, the kit comprising a device comprising at least one electrode for administering an electrical stimulus to opposed leg muscles of a patient; a power supply connectable to the electrode; and a control means for activating the electrode to administer an electrical stimulus to the muscles sufficient to cause the muscles to contract isometrically.

The device described in WO2006/664118 includes certain electrode configurations which may be used. We demonstrate herein data showing specific novel electrode configurations which are perceived as more comfortable by users. The present invention therefore provides a device comprising positive and negative electrodes for administering an electrical stimulus to opposed leg muscles of a patent; a power supply connectable to the electrode; and a control means for activating the electrodes to administer an electrical stimulus to the muscles sufficient to cause the muscles to contract isometrically, wherein one electrode substantially encloses the other.

By "Substantially encloses" is meant that one electrode surrounds at least 66%, preferably at least 75%, more preferably at least 85%, more preferably at least 90%, and most preferably 100% of the perimeter of the other. It is not essential that the one electrode be entirely enclosed by the other, although it is preferred.

It has been determined that this arrangement of electrodes leads to improved perception of user comfort.

Preferably the positive electrode substantially encloses the negative electrode.

In some embodiments the electrodes are in the form of concentric, or substantially concentric, circles. In others, the electrodes are generally elongate, preferably generally quadrilateral, such as rectangular, or C-shaped or U-shaped.

Preferably one electrode has a larger area than the other electrode; preferably the larger electrode is the positive electrode.

Preferably the control means is configured to administer an AC electrical stimulus. Preferably the waveform of the current is asymmetric; conveniently the waveform provides an initial (positive) pulse of large magnitude and short duration, followed by a (negative) pulse of small magnitude and long duration. The area under the curve of the two pulses will be equal. In one embodiment, the initial pulse is of a generally square waveform.

A further aspect of the present invention provides a device comprising positive and negative electrodes for administering an electrical stimulus to a nerve innervating opposed leg muscles of a patient, so as to cause isometric contraction of the muscles; a power supply connectable to the electrodes; and control means for activating the electrodes.

Preferably the positive and negative electrodes are separated by 20-30 mm: we have found that this provides a preferred degree of stimulation.

The electrodes may be of different sizes; preferably the positive electrode is larger than the negative. This provides a higher charge density at the motor point, and greater capacitance overall. The electrodes may be silver electrodes. The electrodes may be continuous, or may include holes—for example, the electrodes may be solid electrodes, or may be in the form of a mesh.

In preferred embodiments, the device comprises a flexible substrate on which are mounted the electrodes, the power supply, and the control means. The control means may be, for example, a PCB configured to activate the electrodes as appropriate. The power supply may be an electrical cell. The substrate is preferably flexible, but not stretchable—this reduces the risk of the electrodes cracking or breaking. For example, the substrate may be a thermoplastic elastomer.

The electrodes may be directly printed onto the substrate, by conventional printing means (for example pad or tampo printing). Similarly, conductive tracks may also be printed onto the substrate if desired.

The substrate may be in the form of an elongate strip or tongue, with the electrodes spaced along the strip. Such an arrangement may require a conductive track to be placed from the power supply, to the further electrode, passing close to the nearer electrode. In such, arrangements, the device may further comprise one or more insulative strips or regions arranged to separate the conductive track from the nearer electrode; insulative strips may, also or instead be arranged along the edges of the strip to prevent current leaking outside the area of the strip. Alternatively, or in addition, the substrate may comprise a recessed groove within which a conductive track may be located; thereby serving to separate the track from the electrode.

In certain embodiments, the device may be configured to be implantable in a patient, for example, implantable subcutaneously. This would be of benefit in chronic indications where long term use of the device is required.

The device further comprises a conductive gel overlying the electrodes. The gel is preferably in a single piece overlying both electrodes, for ease of manufacture as well as structural integrity. We have determined that a single piece of gel may be used, based on the bulk resistivity of the material and geometry, so that leakage resistance is much greater than delivery resistance. Examples of gels which may be used include hydrogel or silicone.

The device may be assembled as follows. The flexible substrate may be produced as a generally flat elongate strip and a recess forming a compartment. The electrodes and conductive tracks are then printed onto the substrate, and the power supply and control means placed into the recess. This serves to connect all the electrical connections. The recess may then be closed, for example, by sonic welding a cover to seal the power supply and control means into the recess. Finally a gel is placed over the electrode s.

The device may further comprise a locating mark to aid correct placement in use.

The device may include a press button for activating or deactivating the device. The control means may be configured to provide a plurality of activation modes (for example, with different stimulation characteristics); the press button may be used to cycle through these modes. The device may include a display means, such as a light or an LED, to indicate the selected activation mode.

Preferably the device is for reducing diastolic flow reversal.

In certain embodiments the device may be disposable; for example, after a single use.

The device is intended to be sufficiently small and light—for example, less than 10 cm in length, and weighing less than 100 g, preferably less than 20 g—so as to be highly portable.

In use the device may be operated so as to engender little or no noticeable skin sensation or discomfort when activated to stimulate muscle contraction.

DETAILED DESCRIPTION OF THE DRAWINGS

Figure 1A:
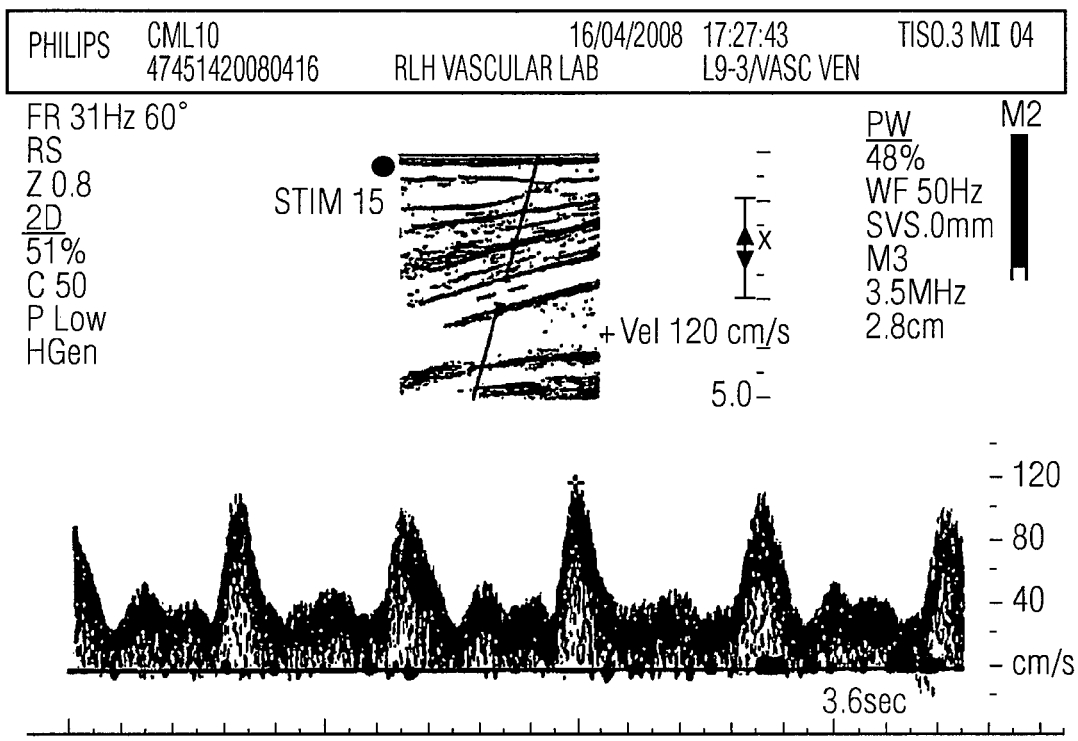
FIGS. 1A through 1C show the measurements of arterial blood flow in a first subject at levels of stimulation of 20 mA, 5 Hz (FIG. 1A); 5 mA, 5 Hz (FIG. 1B); and at no stimulation (FIG. 1C).

A device for electrically stimulating leg muscles is described in detail in WO2006/054118, and the reader is referred to that publication for a full description "of the device. The present invention is primarily based on a number of unexpected effects observed from use of that and similar devices, although we also describe a particularly preferred embodiment of the device.

In brief, though, one embodiment of the device as described in WO2006/054118 includes a loop of elasticated material which, in use, may be worn around a user's lower limb. On the interior surface of the elasticated material are disposed first and second electrodes connected by conductive wires to a cradle which is integral with the elasticated material.

Mounted within the cradle is a control module, which includes a, power cell, a control processor, and an external LED.

The control module is removable from the cradle, with a pair of detents and corresponding recesses allowing the cradle and control module to interlock. The control module and cradle carry, corresponding electrical contact surfaces which provide for electrical communication between the control module and the first and second electrodes via the conductive wires, The control processor includes a timer module, a data store, a program store, and a logic unit.

In use, the device is operated as follows. The elasticated loop is worn on a user's lower limb, such that the first electrode is in contact with the calf muscle at the rear of the limb, and the second electrode is in contact with the anterior muscle of the limb. When the control module is engaged with the cradle, the device is automatically activated.

The program store is preloaded with an operating program arranged to activate the electrodes each minute using a 40 Hz pulsed DC of 20 mA for 0.1 second. Both electrodes are activated simultaneously. The timer module serves to generate appropriate timing signals, while the logic unit executes the program of the program store.

As the electrodes are activated, the user's muscles are stimulated to contract. Contraction of the rear calf muscle, caused by the first electrode, serves to pump blood out of the leg using the calf pump thereby reducing pooling of the blood. Contraction of the anterior muscle, caused by the second electrode, is intended to reduce unwanted movement of the ankle by counterbalancing the contraction of the rear calf muscle. Simultaneously with each activation, of the electrodes, the LED on the outer surface of the control module is also activated; this provides a visual confirmation that the device is operating.

The foregoing is a description of one embodiment of the device. However, a suitable device for stimulating muscles may be assembled from conventional skin, electrodes and a suitable electrical power supply. It is this form of test rig which was used in the following experiments.

Experimental Design

Study Title: A study to determine the effects of a novel method for enhancing lower limb blood flow in Healthy Adult Volunteers.

Objectives: The primary objective of this study was to evaluate the effectiveness of topical electrical stimulation in enhancing lower limb perfusion. The secondary objective was to evaluate with duplex ultrasound and plethysmography techniques the blood flow velocity and volume changes associated with varying the intensity and level of electrical stimulation.

Study Design: One-centre, physiological response study in healthy Volunteers.

Stimulus Application: The effects of electrical stimulation on lower limb blood flow were investigated in healthy volunteers during a 4-hour period of prolonged sitting. Each subject completed his or her study sat in an Industry Standard airline seat. The stimulator used custom stimulation protocols. Superficial electrical stimulation was applied to the lateral popliteal nerve located in the area of the popliteal fossa.

Sample Size: 30 Volunteers

Environmental Conditions

The examinations were carried out in a quiet, stable, draught free environment, both temperature and humidity controlled (24±10 C, relative humidity 30-40%). Volunteers were instructed to have a light breakfast, avoiding fatty foods, tobacco and caffeine and to abstain from vigorous exercise from the previous evening onwards. The volunteers were lightly clad (in shorts), sat in a comfortable position with legs bent at the knees.

The effects of electrical stimulation on lower limb blood flow were investigated in healthy Volunteers during a 4-hour period of prolonged sitting. Each subject completed his or her study sat in an Industry Standard airline seat, which has been specifically obtained for this investigation.

The leg clearance distance was be set at 34 inches, by positioning of a toe-bar. Each subject was positioned in the seat by a safety belt to maintain a close uniformity of posture and actively encouraged to remain as passive as can be tolerated by the individual.

Physiological Assessments

During this phase, the amplitude and frequency of the electrical stimulation was varied and associated changes in blood flow recorded.

Changes in lower limb blood flow were evaluated using routine non-invasive plethysmographic techniques (photoplethysmography, strain gauge plethysmography and air plethysmography), transcutaneous oxygen and where possible, colour flow duplex ultrasound.

Changes in blood flow and volume in response to the protocols were compared to blood flow and velocity changes determined by voluntary muscle action i.e. Volunteers were be asked to perform 10 plantar flexions (10 toe lifting movements—with the heel on the ground). This is the maximum physiological response that can be obtained in the sitting position.

Volunteers were asked to evaluate acceptance and tolerability of electrical stimulation sequences by use of a questionnaire (Verbal Rating Scores) and a scoring index (Visual Analogue Scores). Discomfort was related to normal measurement of blood pressure, measured on the upper arm using a standard sphygmomanometer cuff.

Following the period of sitting for 4-hours Volunteers will be re-examined with duplex ultrasound to recheck the status of the deep veins to exclude the development of significant thrombi. The study was performed on each subject at two separate occasions which were then averaged to reduce experimental bias.

Stimulator

The device produced a range of pre-Set programmed corresponding to different stimulation currents, and pulse frequencies. The waveform was specifically designed for motor nerve stimulation, as opposed to direct muscle stimulation. Pulse amplitudes ranged from 1 mA to 40 mA, with frequencies ranged from 1 Hz to 5 Hz, which is a significant departure from the Physiotherapy and TENS protocols (which generally apply substantively higher currents and frequencies).

We applied a succession of 15 different stimulation programmes to each subject during the course of each study, according to a 2-dimensional matrix of amplitude and frequency, as shown in Table 1. The duration of each stimulation programme was 5 minutes, and will be followed by a 10-minute recovery phase to allow vascular re-equilibration prior to the next sequence.

TABLE 1

| Stimulation sequence | | |
|---|---|---|
| Programme # | Amplitude/mA | Frequency/Hz |
| 1 | 1 | 1 |
| 2 | 1 | 3 |
| 3 | 1 | 5 |
| 4 | 5 | 1 |
| 5 | 5 | 3 |
| 6 | 5 | 5 |
| 7 | 10 | 1 |
| 8 | 10 | 3 |
| 9 | 10 | 5 |
| 10 | 20 | 1 |

TABLE 1-continued

Stimulation sequence

| Programme # | Amplitude/mA | Frequency/Hz |
|---|---|---|
| 11 | 20 | 3 |
| 12 | 20 | 5 |
| 13 | 40 | 1 |
| 14 | 40 | 3 |
| 15 | 40 | 5 |

During each of the 15 programmes, non-invasive blood flow and volume parameters were measured as specified above, with reference to the levels observed during voluntary muscle contraction, and with reference to levels observed in the contralateral limb.

Example 1: Blood Flow Patterns

Figure 1B:
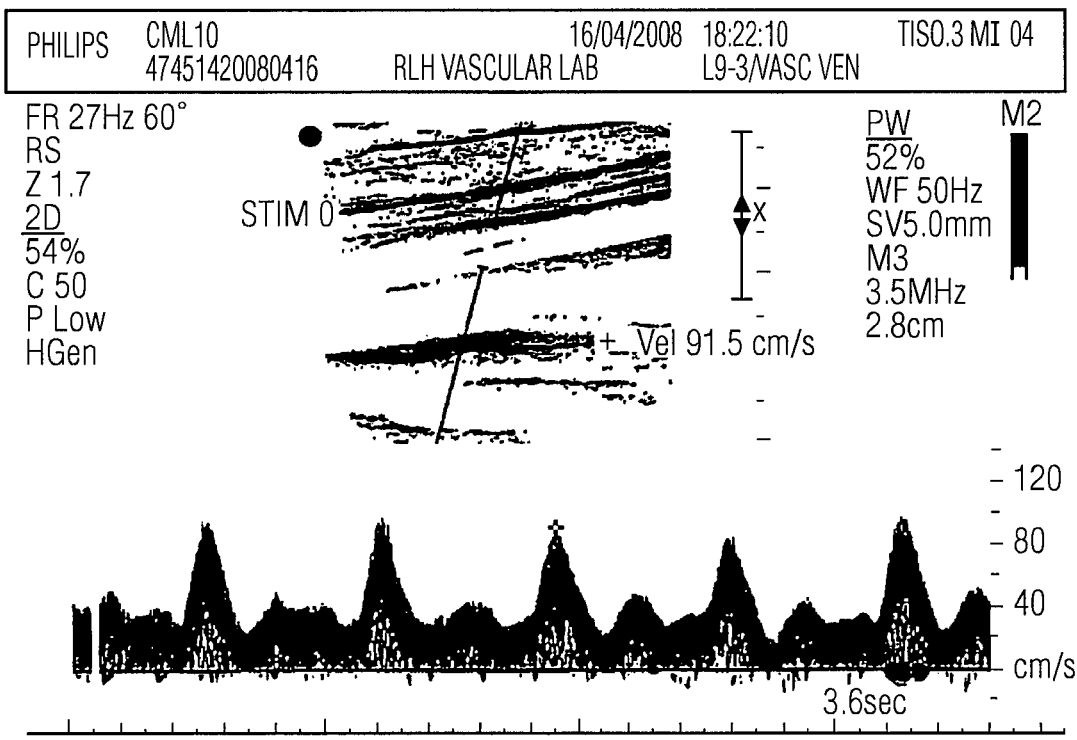
Figure 1C:
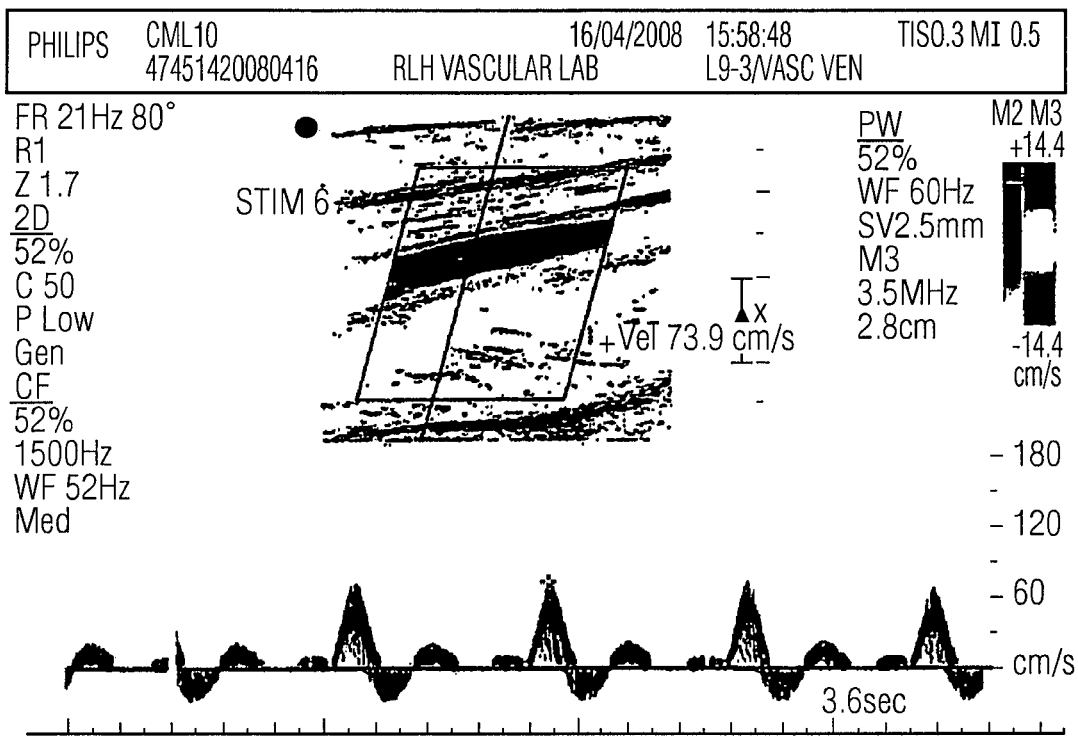
Figure 2A:
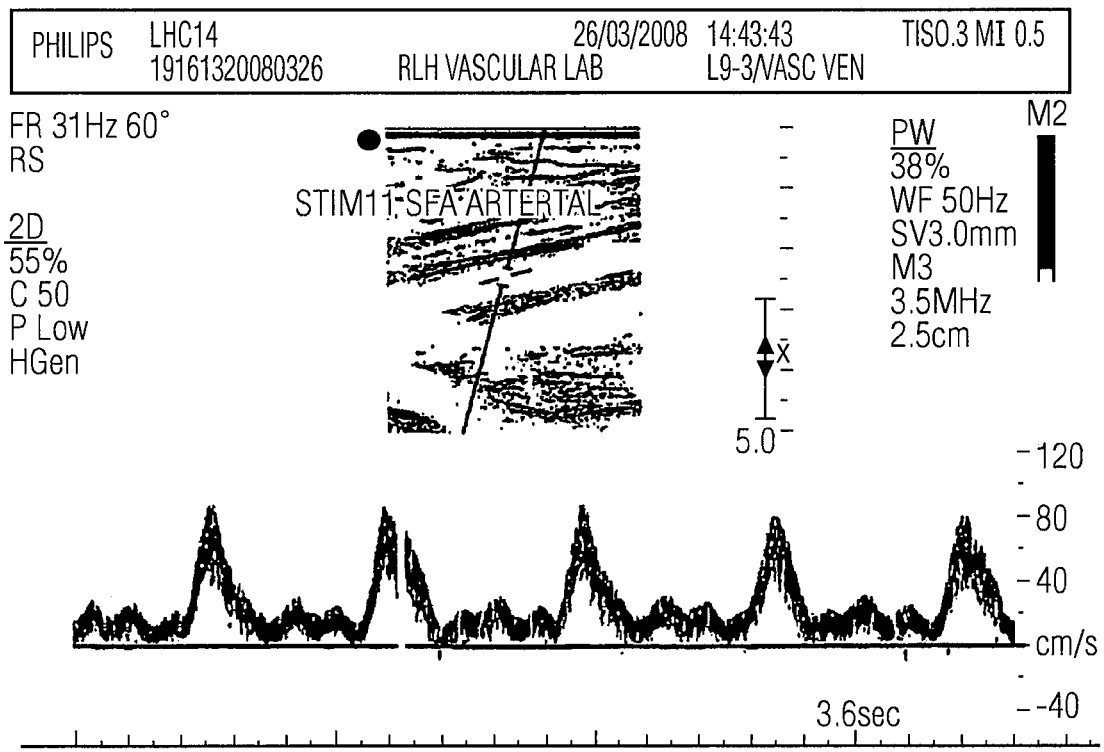
FIGS. 2A through 2C show the measurements of arterial blood flow in a second subject at a level of stimulation of 20 mA, 3 Hz (FIG. 2A); immediately after stimulation (FIG. 2B); and at rest (FIG. 2C).
Figure 2B:
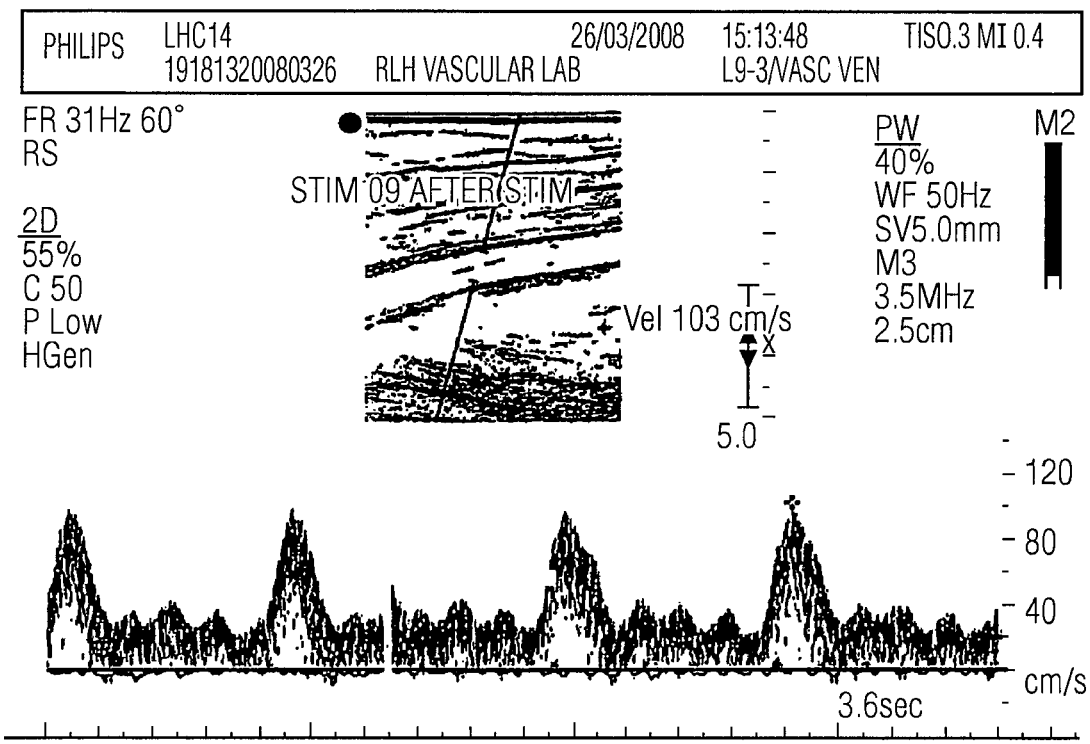
Figure 2C:
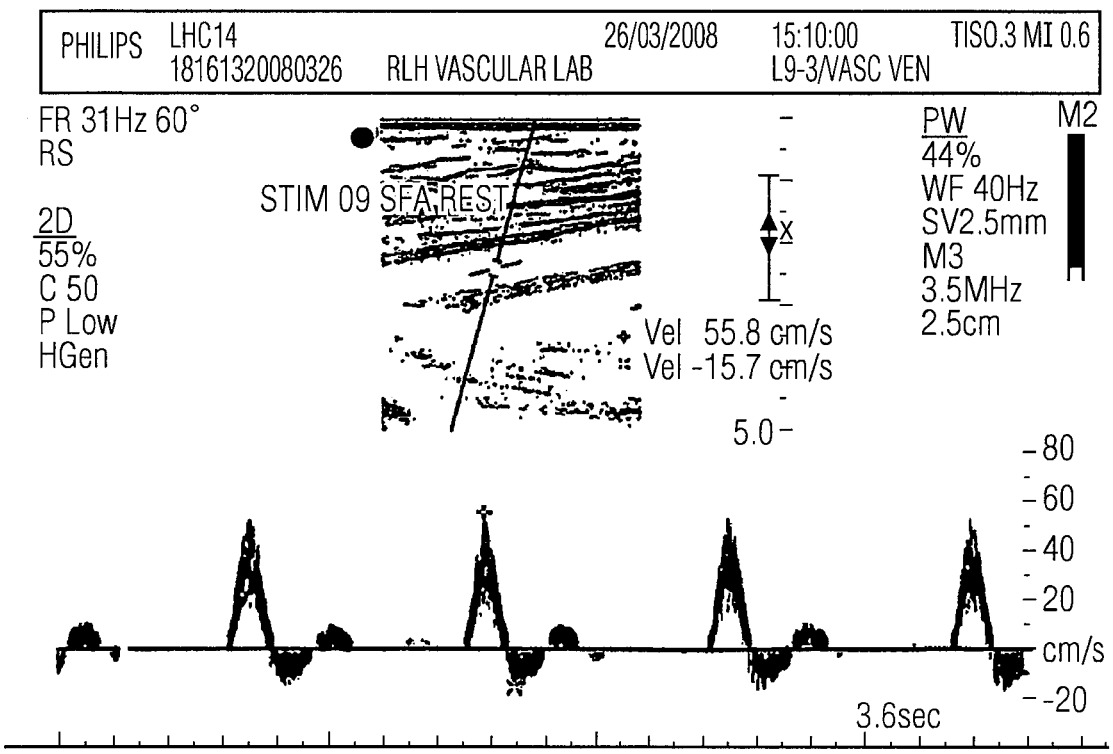
Figure 3A:
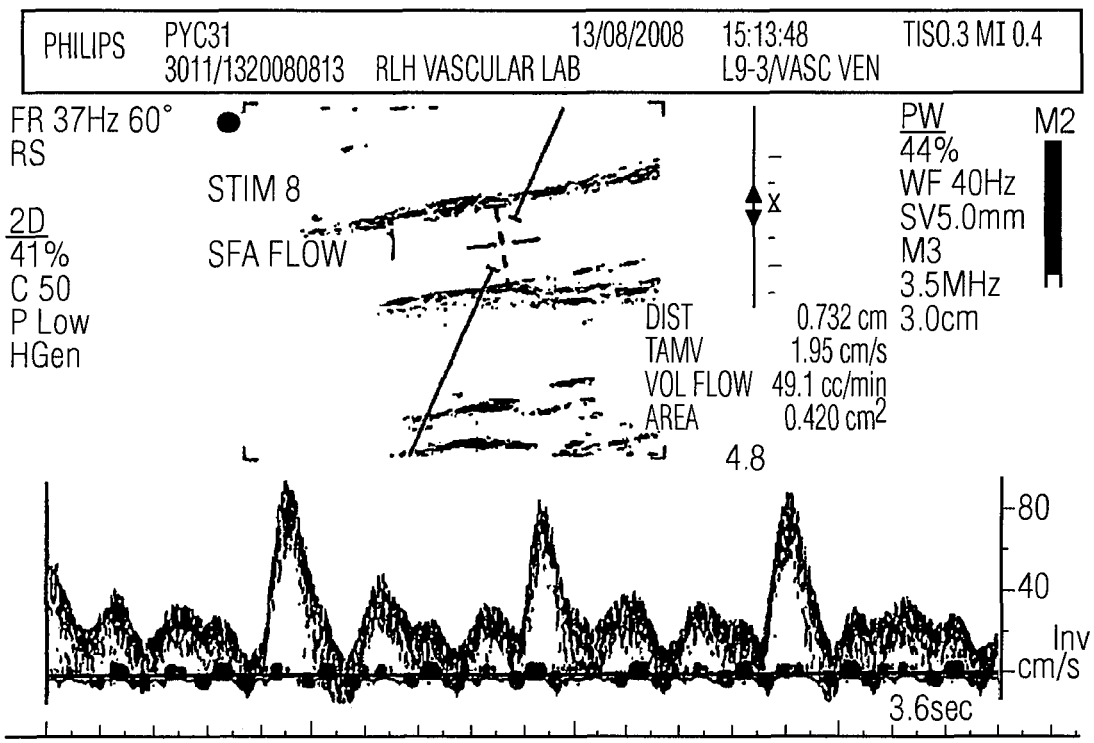
FIGS. 3A through 3F show the measurements of arterial blood flow in a third subject at levels of stimulation of 10 mA, 3 Hz (FIG. 3A); 1 mA, 3 Hz (FIG. 3B); 20 mA, 5 Hz (FIG. 3C); 5 mA, 1 Hz (FIG. 3D); 5 mA, 3 Hz (FIG. 3E); and at rest (FIG. 3F).
Figure 3B:
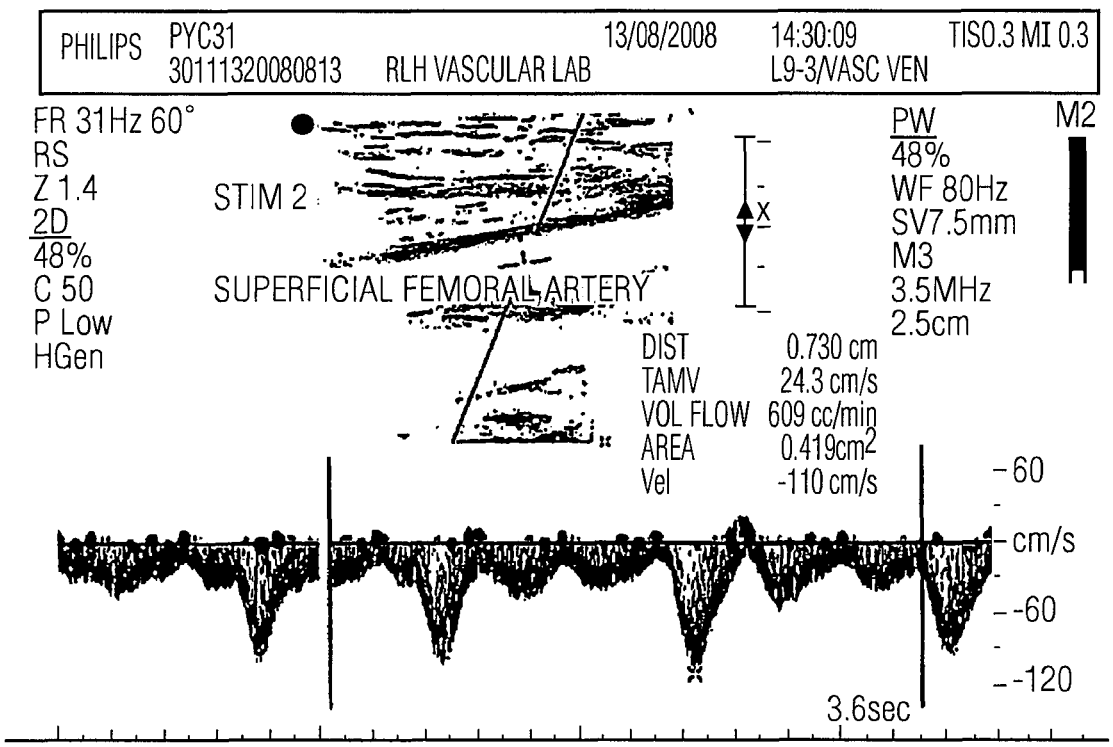
Figure 3C:
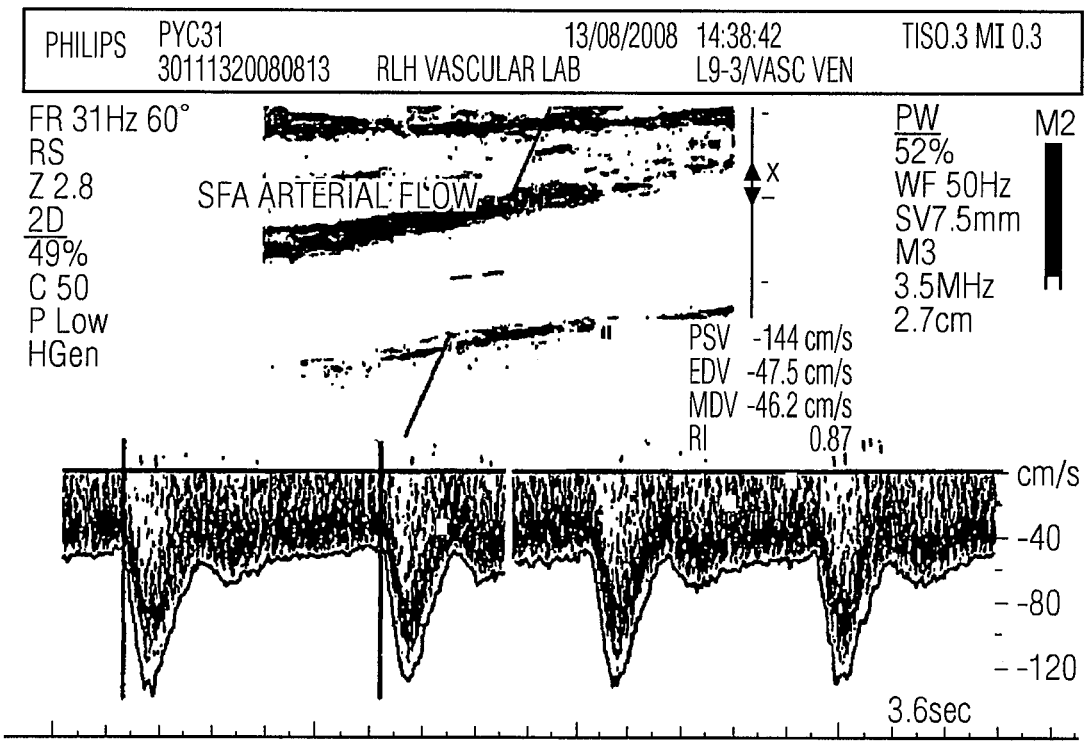
Figure 3D:
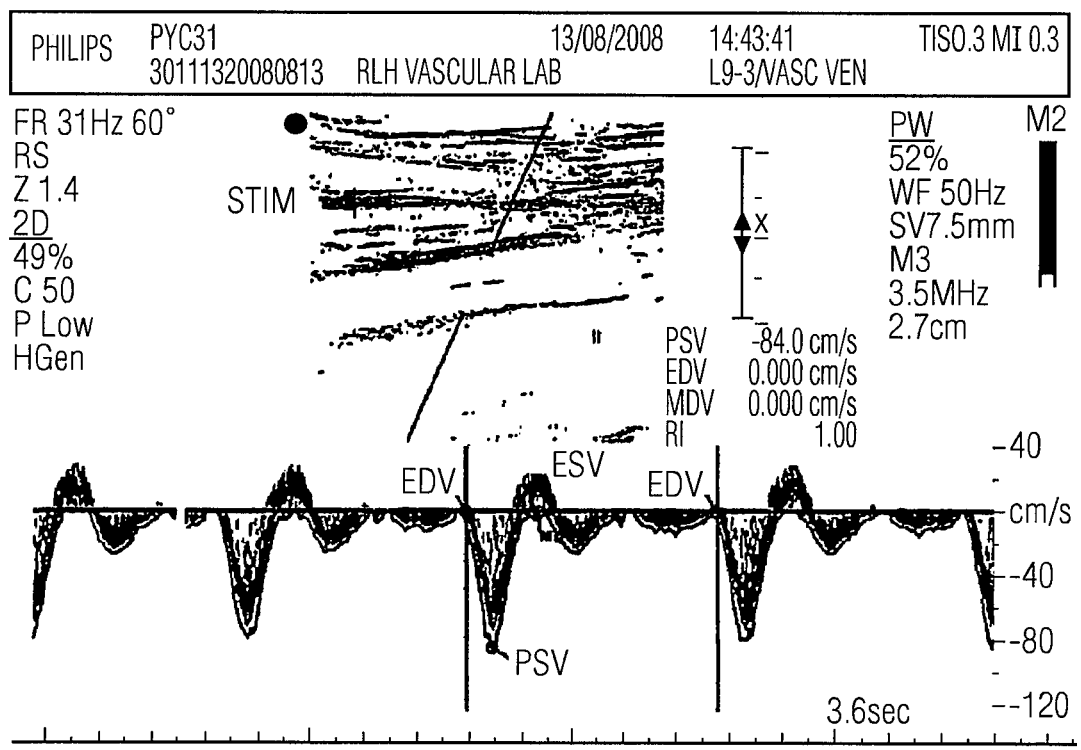
Figure 3E:
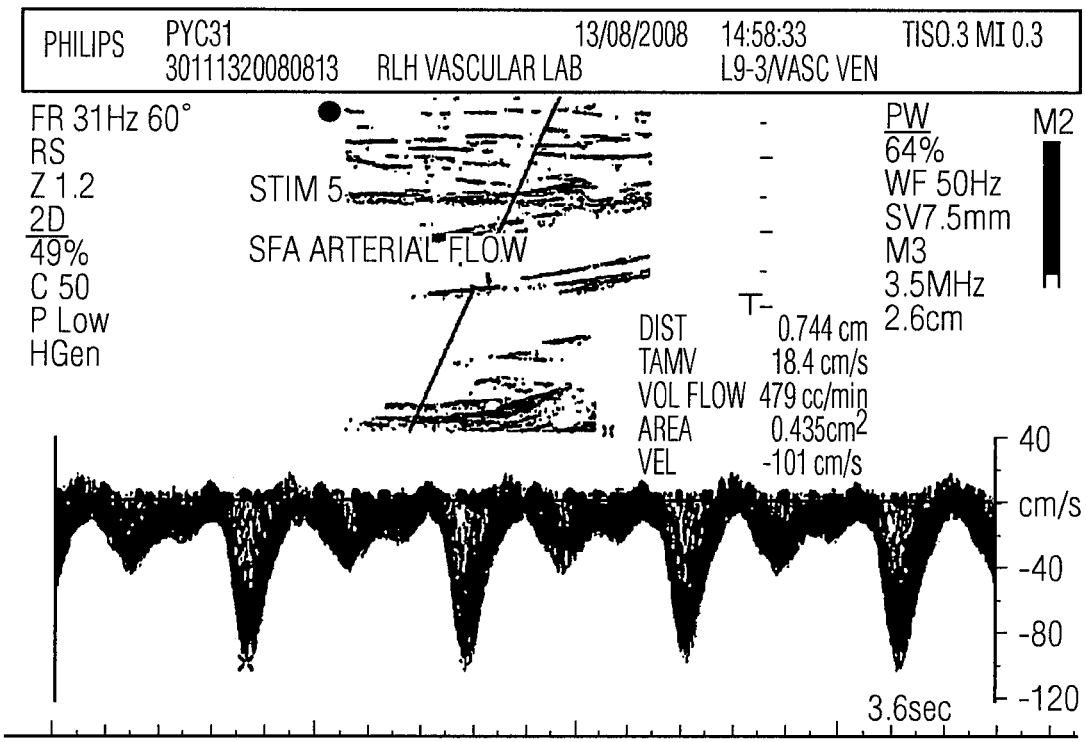
Figure 3F:
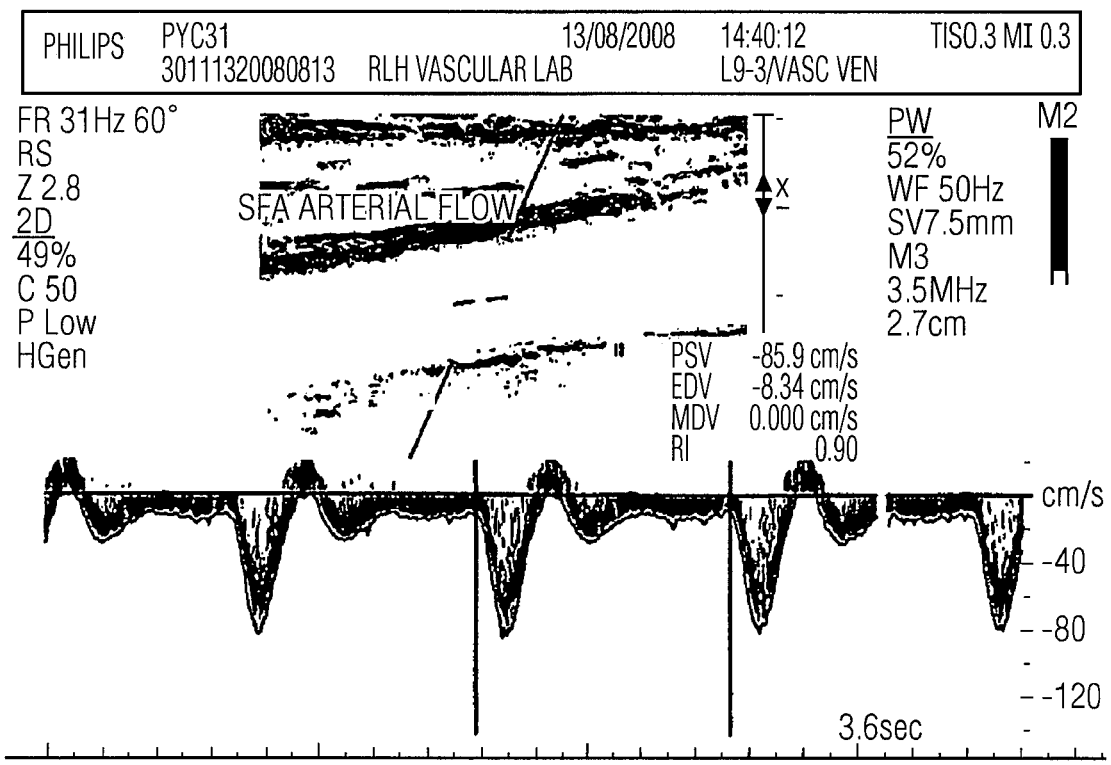

The patterns of venous blood flow in volunteers were monitored using vascular ultrasound of the stimulated leg. Representative examples are shown in FIGS. 1-3, FIG. 1a shows stimulation in a first subject at 20 mA, 5 Hz; FIG. 1b at 5 mA, 5 Hz; and FIG. 1e with no stimulation. FIG. 2a shows a second, subject stimulated at 20 mA, 3 Hz; FIG. 2b the same subject immediately after stimulation; and FIG. 2c the subject at rest. FIG. 3a shows a third subject undergoing stimulation at 10 mA, 3 Hz; FIG. 3b at 1 mA, 3 Hz; FIG. 3c at 20 mA, 5 Hz; FIG. 3d at 5 mA, 1 Hz; FIG. 3e at 5 mA, 3 Hz; and FIG. 3f the subject at rest.

In these examples there was a four-fold increase in venous blood flow velocity from baseline. There was also a significant increase in frequency of cephalad (toward the head) venous blood flow with application of the stimulus.

Flow velocity in the superficial femoral artery doubles and, the reverse flow components of the pulse wave arterial flow waveform are completely abolished with application of the stimulus.

Reverse flow in the superficial femoral artery is due to high resistance of the peripheral vessels; therefore forward flow throughout the cardiac cycle suggests a significant reduction in peripheral vascular resistance.

A fall in total peripheral resistance (consequent of the increase in vascular pump activation by the device) may be illustrated by the laser Doppler and vascular venous vessel ultrasound blood flow increases. The consequence of this is that cardiac output tends to increase. We have also shown that there is no significant increase in the heart rate (beats per minute). This may be demonstrated by the increase in the arterial blood flow and the change in the waveform.

Importantly the increases in blood flow in the various tissues in the leg are proportionate, and therefore there is an increase in blood flow in all of the tissues; hence no 'steal' of blood from any adjacent tissue. All tissues, skin, muscle, bone etc have increased perfusion of blood.

Resistance of blood flow can influence arterial pressure, cardiac output, distribution of cardiac output to systemic organs, distribution of organ blood flow to the various organ tissues, partitioning of tissue blood flow between capillaries and arteriovenous anastomoses, capillary hydrostatic pressure, and the distribution of blood flow within the cardiovascular system. All of which, are, upregulated by the device at certain, defined settings.

A parallel is in exercise, where the total peripheral resistance also decreases as work load, measure by oxygen consumption increases. The fall in vascular resistance is accompanies by a progressive increase in cardiac output. The device mimics this event without a substantive increase in workload and hence minimal oxygen consumption compared to exercise.

Increases in microcirculatory blood flow may additionally be explained by an increased utilisation of previously closed or 'resting' capillary networks, which become available for local exchange. The effect of this is a greatly increased tissue perfusion and a further effect on peripheral vascular resistance.

This is a novel and unique observation, which has significant impact on the cardiovascular system and vascular therapeutics.

Thus, application of the electrical stimulus can increase venous blood flow, and can reduce or prevent diastolic flow reversal in the artery. Note that this does not occur at all settings; FIG. 3d shows no flow reversal when stimulated at 5 mA, 1 Hz.

This effect has the potential for a wide range of therapeutic and diagnostic applications. For example, as the effect only occurs at certain settings, it is likely that the current and frequency at which it appears in individual patients may be characteristic of their normal arterial flow and/or peripheral vascular resistance. This may be used to diagnose the presence and/or severity of circulatory disorders in a patient. Therapeutically, the modified arterial flow and reduced peripheral vascular resistance may be of benefit in treatment of a range of conditions, including ischaemia, cardiac vessel disease, ulceration, and so on.

Example 2

Figure 4:
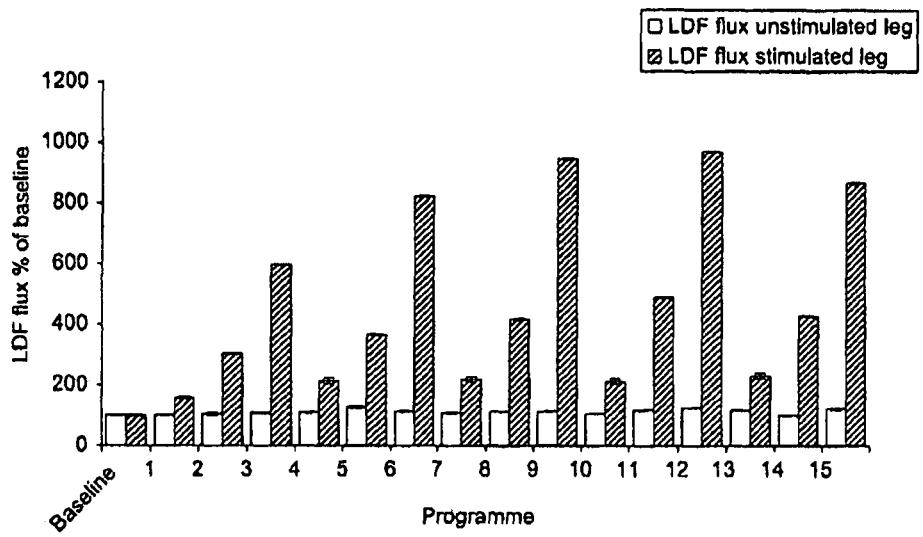
FIG. 4 compares the speed of skin blood flow in stimulated and unstimulated limbs at different levels of stimulation.

Laser Doppler Fluxmetry (LDF) was used to measure the speed of skin blood flow; the results are shown in FIG. 4. LDF flux (speed of blood) is increased up to ~1000% in stimulated leg compared to baseline and the unstimulated leg, which showed values only around baseline level.

Example 3

Figure 5:
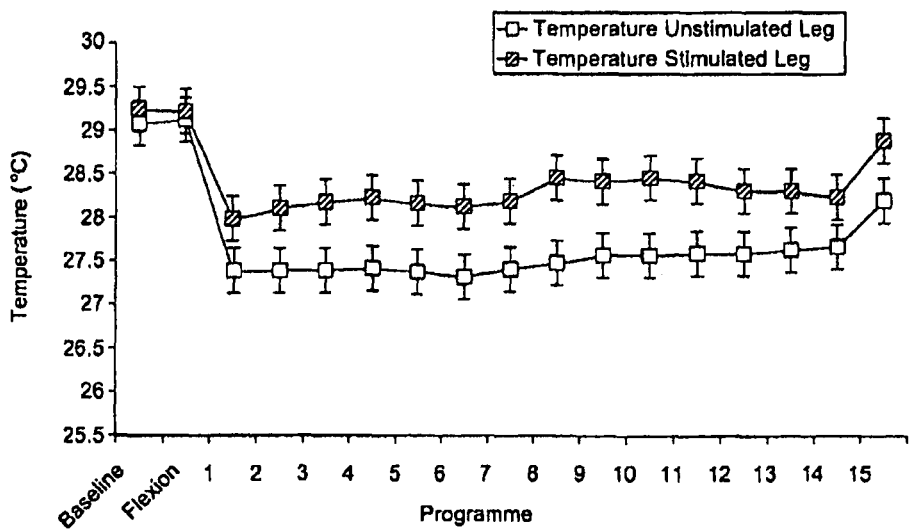
FIG. 5 compares skin temperature in stimulated and unstimulated limbs at different levels of stimulation.

Skin temperature was measured in stimulated and unstimulated legs; the results are shown in FIG. 5. There is a slight increase in temperature at all stimulations in the stimulated leg compared to unstimulated leg. Temperature in the body is generated by metabolism and blood flow. As the metabolism is not altered during the stimulations the slight increase in skin temperature is an indicator for increased blood flow in superficial layers of the skin.

Example 4

Therapy for Osteoporosis

Every year there are approximately 2 million osteoporotic fractures worldwide. (in 1990 there were 1.66 million, and 6 million per year forecast by 2050 according to World Health Organisation). High-risk groups include the elderly population, and people with spinal cord injuries.

In the healthy individual, bone is constantly being remodeled according to physical requirements. Osteoclast cells remove minerals from bone, allowing collagen matrix to resorb, while osteoblasts lay down new collagen matrix and mineral deposits.

Various theoretical models have been proposed over the last century for the mechanism by which the body controls bone density. Wolff, in 1892, proposed that bone deposits followed the patterns of stress in the bone. Frost's 1987 "mechanostat" theory suggested that bone was maintained to maintain uniform strain under habitual loads.

Models for explaining why some individuals developed problems with maintaining bone density initially focused on disuse. In the ageing individual, decreasing use of the bone leads to lower doses of the stresses and strains required to signal bone maintenance. More recently, however, it has been suggested that there is a vascular component to the etiology. Osteoporosis appears to occur in individuals with impaired bone perfusion, either by reduced angiogenesis (itself aggravated by disuse), atherosclerosis restricting flow in existing vessels, or simply lower activity levels causing less blood circulation. (Trueta J. The role of the vessels in osteogenesis. J Bone Joint Surg Br. 1993).

The present invention has the potential to mitigate vascular risk factors for osteoporosis, by increasing perfusion of bone. This can help in two ways. Firstly, augmenting blood supply overcomes limitation of bone modelling caused by reduced perfusion. Secondly, pharmaceutical interventions for osteoporosis can be delivered more effectively to the bone by improving bone perfusion.

A study carried put under the supervision of the inventors has demonstrated that 1) Blood flow in the tibia and femur are enhanced when the device is active; and 2) Perfusion indices indicate that the bone is less hypoxic when the device is active.

Figure 6:
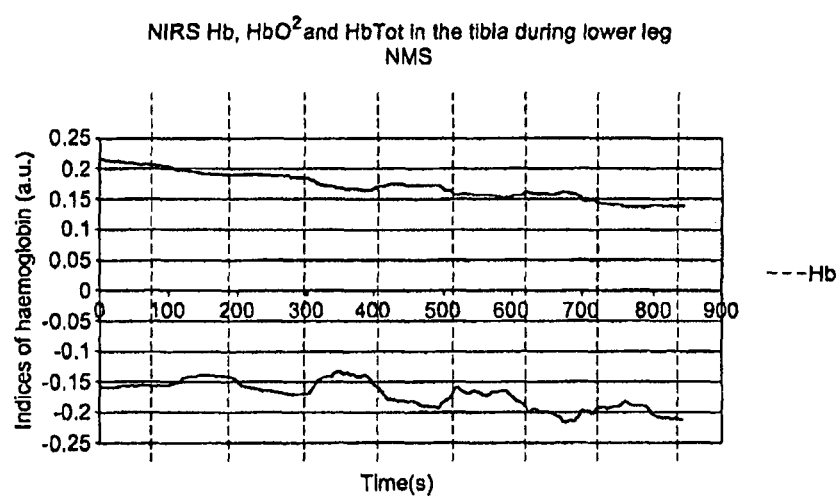
FIG. 6 shows oxyhemoglobin levels measured by infrared spectroscopy in the tibia during stimulation cycles.

FIG. 6 shows Oxyhaemoglobin level measured by infrared spectroscopy in the tibia, during stimulation cycles (100 seconds on, 100 seconds off). Total blood content (top line) drops during stimulation, indicating that the calf pump aids evacuation, and that oxyhaemoglobin levels, rise during stimulation, indicating better oxygenation (reduced hypoxia).

Figure 7:
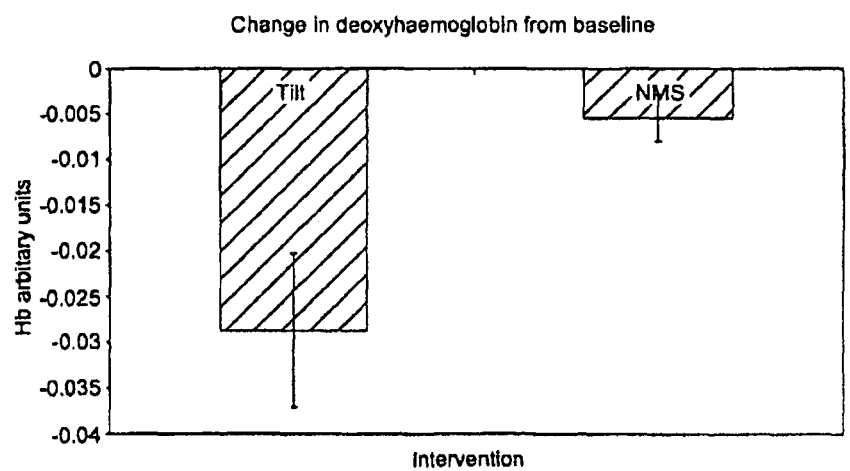
FIG. 7 shows the change in deoxyhemoglobin levels in all patients during stimulation.

FIG. 7 shows the results for 12 subjects summated, showing the mean and standard deviation reduction of deoxyhaemoglobin relative to baseline. The device (labelled NMS) on the chart shows a significant reduction when active. As an idea of scale, this is compared with the reduction achieved by augmenting blood supply using the tilt-table method. This is a known hydrostatic step-change, which consists of the subject lying supine on a tilt table, and while strapped to the table they are tilted into a standing upright position, providing a very large hydrostatic vascular stimulus. This chart may be considered analogous to comparing DVT parameters with the device to foot flexion.

The foregoing examples indicate that the device and method may be used to address new clinical targets. These include:
Lower limb arterial disease—Peripheral Arterial Disease
Enhanced lower limb lymphatic drainage.
Cardiac diseases
Fractures
Enhancement of bone marrow perfusion—for example the management of sickle cell crises, ischaemic bone marrow, stem cell and bone marrow harvest procedures—as well as improving treatment of cancers by delivering drugs to the bone Marrow.
Soft tissue injury of the lower limb—skin and muscle bruising and micro tears.
Sports training and rehabilitation.
Restless Leg Syndrome (Wittmaack-Ekbom's syndrome)
Enhancement of endothelial-derived nitric oxide and prostacyclin release.

Example 5

Discomfort

Neuromuscular stimulation is commonly used to elicit muscle activity for several different applications. These include exercise, rehabilitation and restoration of function (eg drop foot stimulator) and more recently augmentation of blood supply using the soleus pump for various purposes, NMS has commonly been used previously for restoration of function in insensate individuals, eg with spinal cord injury. In these users, discomfort or pain associated with the stimulation is not an issue.

In the sensate user, however, discomfort or pain during stimulation is an issue, and sometimes a limiting factor in the level of stimulation applied.

In NMS, an electrical stimulus is used to cause contraction of a system of skeletal muscles. Unfortunately, efferent (motor) and afferent (sensory) nerves are typically bundled together in the same nerve conduit, and additional sensory nerves are present in the skin. This means that, as well as stimulating motor nerves, NMS causes some stimulation of sensory nerves. If sensation signals arrive at the brain, in large numbers and rapid succession, they may be perceived as pain in some individuals.

Relationships have been found between electrode size and stimulatory response. It has also been found that stimulation quality and tolerance are sensitive to electrode position. These relationships have now been investigated further by the inventors, in a series of experiments.

One hypothesis tested was that smaller electrodes would be better tolerated, since they allow us to target accurately the region of the peroneal lateral popliteal, without unnecessary stimulation of surrounding areas of skin receptors. This was not found to be reliably the case in our experiments. This finding may be rationalised as follows.

Current density is usually maximal at the skin/electrode interface, whereas the quality of muscle contraction is determined by the current density at the point of excitation.

For a given current, a smaller electrode provides increased current density at the skin. However, this does not necessarily translate to maximal current density at the point of excitation. The electrodes are necessarily spaced from each other to avoid short circuit Charge flows through the tissues from one electrode to the other electrode in a plurality of indirect routes. Therefore the charge takes a wider path in the tissue than at the interface between electrode and skin, with the effect that the charge density is at its highest in the skin, and lower within the tissue, and at the excitation point of the nerve.

Experiments were conducted with various arrangements of electrodes to allow smaller differentials between current density at the skin interface and at the desired stimulation point.

It has been found advantageous to have two electrodes of different size. Since excitation of the nerve is achieved by depolarising the nerve (which normally has a positive extracellular charge and a negative intracellular charge) it is the negative electrode (cathode) that causes the nerve to achieve action potential. It is found to be advantageous to position a small cathode in the precise region to be stimulated, and a larger anode at a site somewhat, removed, allowing high current density at the stimulation site only, and low current density (below action potential) generally.

Figure 8:
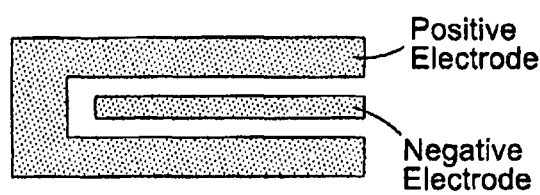
FIG. 8 shows a first desired electrode arrangement.
Figure 9:
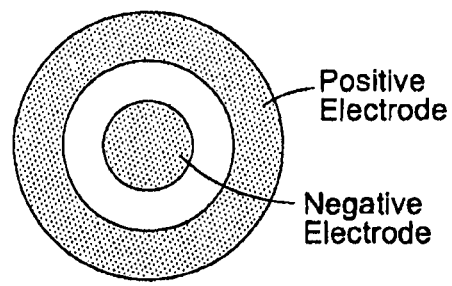
FIG. 9 shows a second desired electrode arrangement.

A refinement to this technique is to provide anodes either side of the cathode, giving a much wider spread of (accordingly lower) charge density at the anodes. Two possible embodiments of electrodes include three parallel strips (centre negative)—see FIG. 8—and target (bull's-eye negative)—see. FIG. 9. The target variant may have a closed or open outer circle, and, may be oval.

The electrode structures were tested experimentally.

Ten normal healthy subjects were used, ranging in age between 24 and 50. A Visual Analog Score was measured by asking each subject to draw a mark on a standard 10 cm line segment, representing where their sensation was on a scale from no discomfort (far left) to extreme pain (far right). A system was adopted for normalising these scores relative to a standard sensation, which was taken to be the existing electrode configuration and waveform used in the previous studies.

Figure 10:
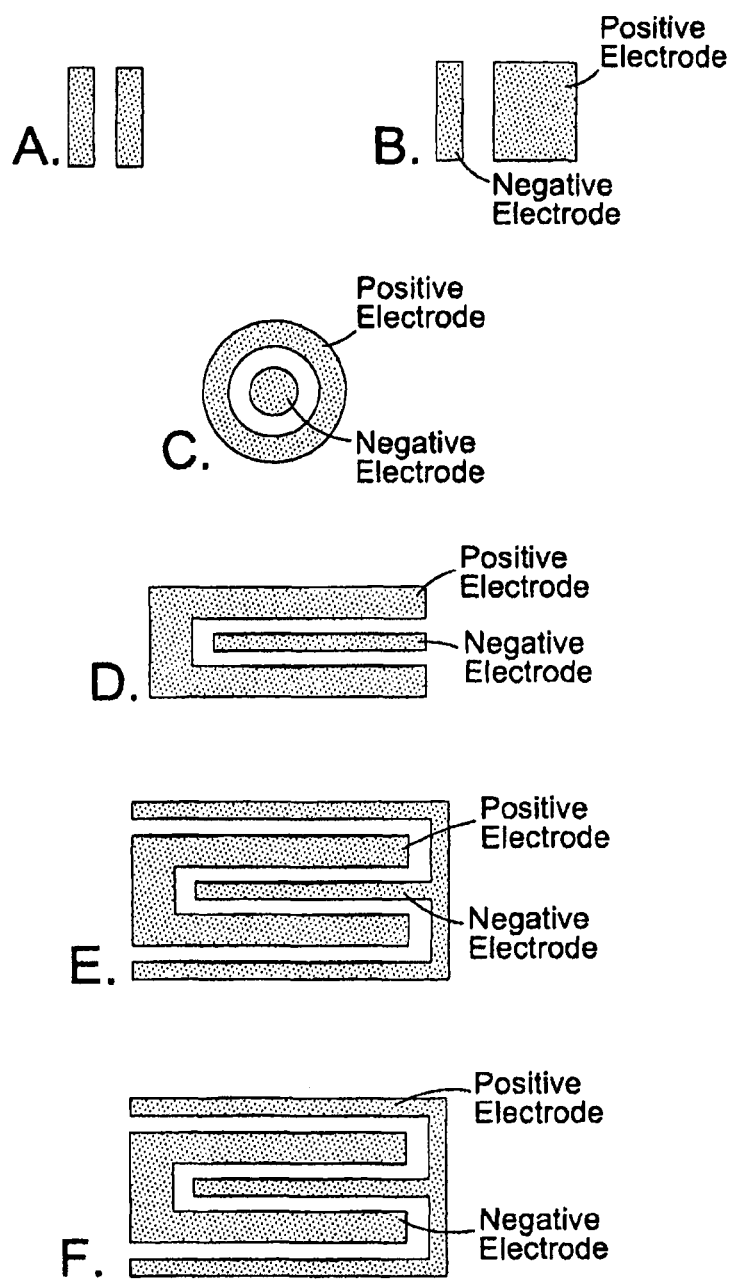
FIG. 10 shows several electrode arrangements tested.

A normalised discomfort score was then derived for each configuration based on the horizontal distance between the VAS for this configuration and the VAS for the standard configuration. Thus, a positive score will indicate less comfortable, and a negative score will indicate more comfortable, FIG. 10 (A-F) describes the electrode configurations used.

Figure 11:
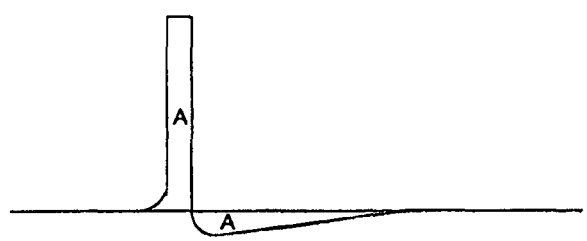
FIG. 11 shows asymmetric and symmetric waveforms tested.
Figure 11:
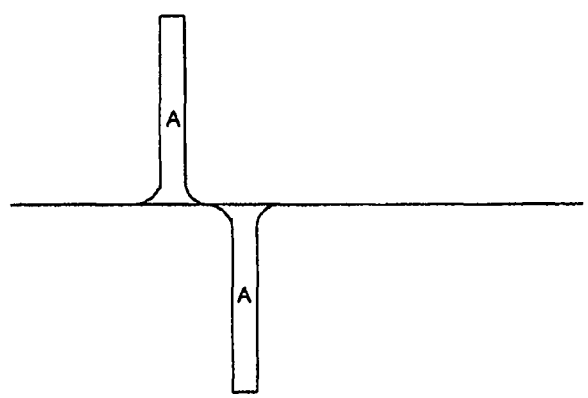

Two waveforms were used, symmetric and asymmetric (see FIG. 11). In both cases, the overall charge is balanced (area A is equal), so no galvanic irritation is possible.

Table 2 gives the key to the electrode/waveform combinations used.

TABLE 2

| Config | Electrode configuration | waveform |
| --- | --- | --- |
| 1 | A | Asym |
| 2 | A | Sym |
| 3 | B | Asym |
| 4 | B | Sym |
| 5 | C | Asym |
| 6 | C | Sym |
| 7 | D | Asym |
| 8 | D | Sym |
| 9 | E | Asym |
| 10 | E | Sym |
| 11 | F | Asym |
| 12 | F | Sym |

Figure 12:
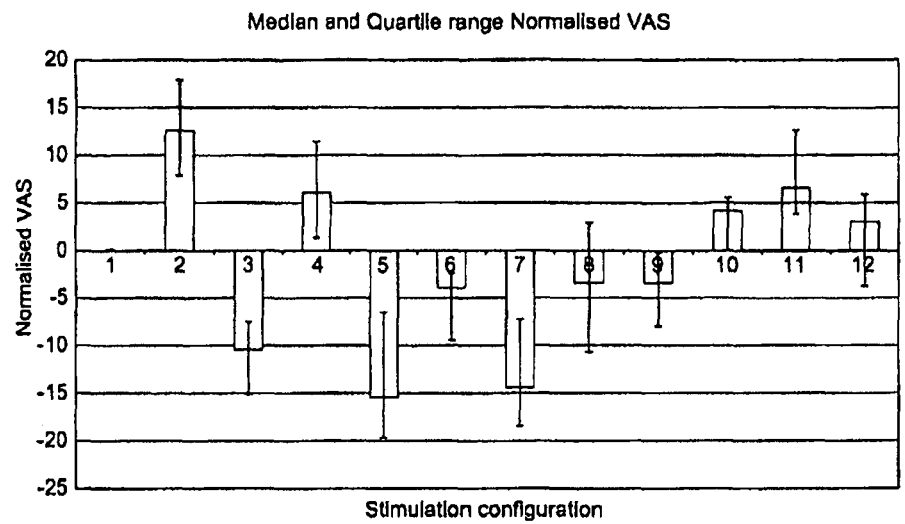
FIGS. 12 and 13 show results from electrode and waveform comfort testing.

FIG. 12 shows each stimulation configuration as a number on the x axis. For each, the median normalised VAS is shown as a blue bar, with the range between first and third quartiles shown as whiskers.

It can be seen that the most preferred combinations are C, D, and to a lesser extent B, all with the asymmetrical waveform.

Note that configuration 1 shows a shore of 0 in every case by definition.

Figure 13:
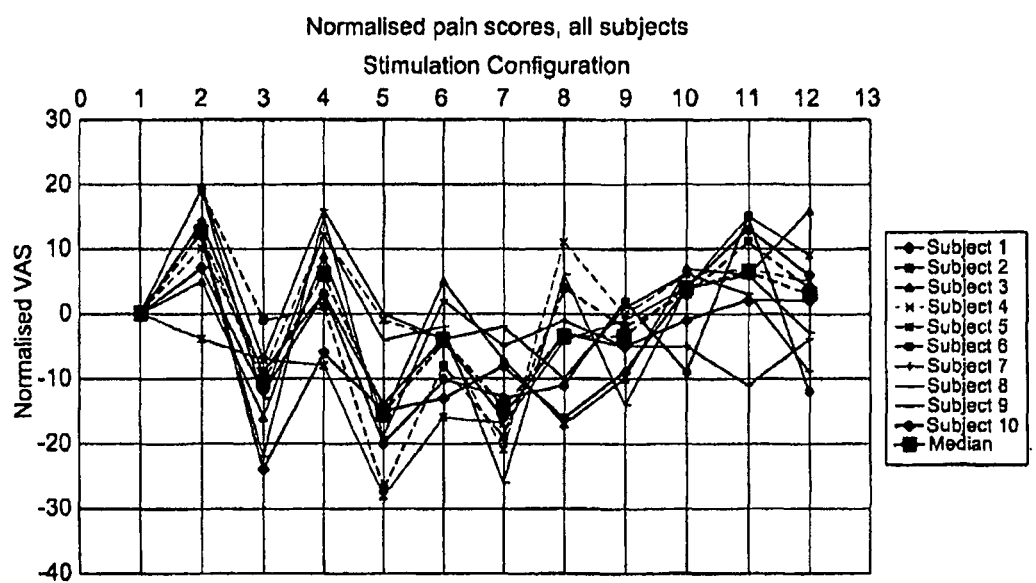
Figure 14:
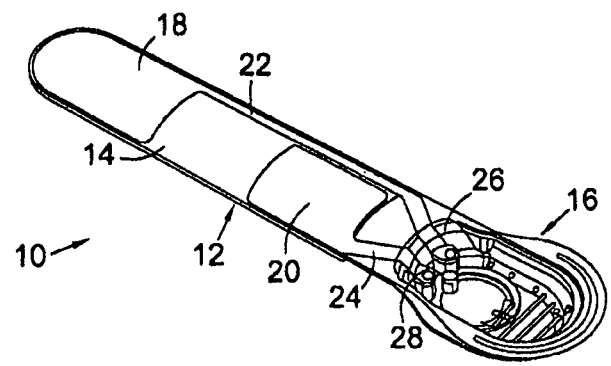
FIGS. 14 to 17 show views of an embodiment of a device according to the present invention.
Figure 15:
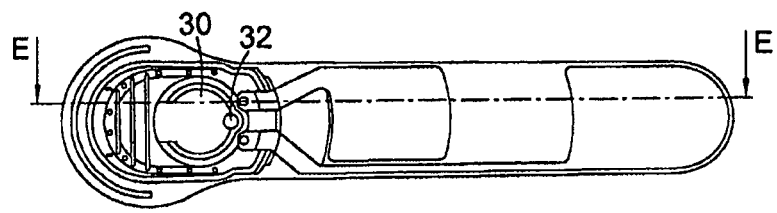
Figure 16:
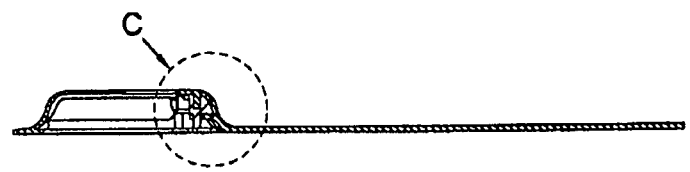
Figure 17:
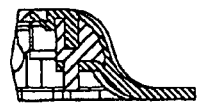

FIG. 13 shows the Normalised VAS ratings for each subject as a separate coloured line. This representation makes still more obvious the preference for the asymmetrical waveform.

Optimal configuration is the symmetrical/target arrangement, negative electrode in the middle, and positive larger than negative. Waveform findings indicate that asymmetrical but charge-balanced (large positive spike followed by smaller but longer duration negative current) is optimal for comfort.

A preferred embodiment of a device according to the invention is shown in FIGS. 14 to 17. The device 10 comprises a flexible, non-stretchable thermoplastic elastomer substrate 12 which includes an elongate tongue 14 at one end, and a moulded recess 16 at the other.

On the tongue 14 are printed positive 18 and negative 20 electrodes. The positive is slightly larger than the negative. Each electrode includes a conductive track 22, 24 leading from the electrode to a respective contact point 26, 28 located in the recess 16.

Not shown in the figures are an insulative strip arranged between the positive track 22 and the negative electrode 20, and similar strips at the edges of the tongue, to prevent unwanted leakage of current.

Within the recess 16 are placed an electrical cell (not shown), and a PCB (not shown) including suitable circuitry to control the electrodes. Together with the conductive tracks 22, 24 and contact points 26, 28, this forms a complete circuit. A plastic cover is then sonically welded over the recess 16 to seal the components. A layer of gel is then placed over the whole device 10; this provides an electrical contact with a user's limb and helps keep the device adhered to a user. The gel may be protected in transit by a peel able backing layer.

The outer surface of the recess 16 is formed with an integral diaphragm button 30 and an aperture 32 for displaying an LED. The button 30 is arranged to contact a corresponding button on the battery housing or PCB to activate the device. The aperture 32 displays an LED which indicates whether the device is operating.

The invention claimed is:

1. A method of reducing or preventing diastolic flow reversal in an artery in a leg of a patient comprising:
administering an electrical stimulus having a frequency of from 1 to 3 Hz and a current of between 0 to 100 mA by means of a single negative surface electrode and a single positive surface electrode to a nerve innervating opposed leg muscles sufficient to cause isometric contraction of the muscles, and wherein, in said method, said electrical stimulus is administered to only one nerve wherein the nerve is stimulated from a single stimulation point and wherein said single negative surface electrode is located at said single stimulation point, and wherein the single positive surface electrode is shaped and positioned so as to provide the single positive surface electrode either side of the single negative surface electrode, thereby reducing or preventing diastolic flow reversal in an artery in a leg of a patient.

2. The method of claim 1, wherein the electrical stimulus has a frequency of 1 Hz.

3. The method of claim 1, wherein the electrical stimulus has a current of 15-30 mA.

4. A method of reducing or preventing diastolic flow reversal in an artery in a leg of a patient comprising:
administering an electrical stimulus having a frequency of 1 Hz and a current of between 0 to 100 mA by means of a single negative surface electrode and a single positive surface electrode to a nerve innervating opposed leg muscles sufficient to cause isometric contraction of the muscles, wherein said single positive surface electrode is larger than said negative single surface electrode and said single positive surface electrode is shaped and positioned so as to provide the single positive surface electrode either side of the single negative surface electrode, and wherein, in said method, said electrical stimulus is administered to only one nerve wherein the nerve is stimulated from a single stimulation point and wherein said single negative surface electrode is located at said single stimulation point, thereby reducing or preventing diastolic flow reversal in an artery in a leg of a patient.

* * * * *